United States Patent [19]

Kondou et al.

[11] Patent Number: 5,021,888
[45] Date of Patent: Jun. 4, 1991

[54] MINIATURIZED SOLID STATE IMAGING DEVICE

[75] Inventors: Yuu Kondou, Kanagawa; Mamoru Izumi, Tokyo, both of Japan

[73] Assignee: Kabushiki Kaisha Toshiba, Kawasaki, Japan

[21] Appl. No.: 284,610

[22] Filed: Dec. 15, 1988

[30] Foreign Application Priority Data

Dec. 18, 1987 [JP] Japan ............................... 62-318664
Dec. 18, 1987 [JP] Japan ............................... 62-318665
Dec. 18, 1987 [JP] Japan ............................... 62-318666

[51] Int. Cl.⁵ ........................................... H04N 3/14
[52] U.S. Cl. .................................. 358/213.11; 358/98
[58] Field of Search ................. 358/93, 98, 213.11, 358/209

[56] References Cited

U.S. PATENT DOCUMENTS 4,660,277  4/1987  Tei ..................................... 437/226
4,684,974  8/1987  Matsunaga et al. ................ 357/68
4,779,130  10/1988  Yabe .................................. 358/98
4,831,456  5/1989  Takemura ........................... 358/98

FOREIGN PATENT DOCUMENTS 62-281361  12/1987  Japan.

Primary Examiner—Stephen Brinich
Attorney, Agent, or Firm—Oblon, Spivak, McClelland, Maier & Neustadt

[57] ABSTRACT

The invention is concerned with the miniaturization of construction of solid state imaging devices used in electric cameras, endoscopes or the like. A flexible printed circuit board assembled with some peripheral components thereon is attached to a side surface of a solid state imaging element to expose the element directly to incident light. The element is composed of a CCD chip and a light transparent cover sized about same as the CCD chip, and both are electrically connected using conduction bumps.

8 Claims, 6 Drawing Sheets

MINIATURIZED SOLID STATE IMAGING DEVICE

BACKGROUND OF THE INVENTION

This invention relates to a solid state imaging device, and more particularly to a solid state imaging device used in an improved assembling structure for a subminiature electronic camera and an electronic endoscope or the like.

Recently, the electronic endoscope and the microcamera, etc., have been developed as applied products using the solid state imaging device A fine tip portion for the endoscope to be inserted into a human body, and a small size for the camera-head of the micro-camera are important salespoints with these products. Therefore, it is desirable for the solid state imaging device assembled therein to be as small as possible. This solid state imaging device is composed of peripheral circuit components, including a noise reduction circuit or an amplification circuit, etc., and extension cables. The external diameter of the tip portion of the electronic endoscope has a direct influence upon the size of the solid state imaging device. As a result there has been an effort to miniatuarize the size of the solid state imaging device.

An example of a typical conventional solid state imaging device assembled in an electronic endoscope is shown in FIG. 11. A solid state imaging element 61 is disposed on a flexible printed circuit board (FPC) 62. Peripheral circuits constructed by chip components 63 are assembled adjacent to the solid state imaging element 61 on the FPC 62. The solid state imaging element and a picture signal processing circuit are connected using and an extension cable of one or more meters. Therefore, minimum necessary peripheral circuits, such as a noise reduction circuit, and a picture amplification circuit etc., must be disposed close to the solid state imaging element 61. In the electronic endoscope, an observation system including lenses to focus the image on the solid state imaging element and in addition, a light guide for a lighting system and a treating channel must be accommodated usually into a flexible tube. Further, the flexible tube must be fine size.

The solid state imaging element 61 is composed of chip carriers 70 made of ceramic, a CCD (charge coupled device) element 66 and a light transparent cover 67 made of optical glass. A cavity 68 is provided on the chip carrier 70. Connection patterns (not shown) are provided surrounding the cavity 68 of the chip carrier 70. The CCD element 66 is disposed in the cavity 68. Electrodes (not shown) of the CCD element 66 and the connection patterns (not shown) of the chip carrier 70 are bonded using fine metal wires 69. Thus, the solid state imaging element 61 and the FPC 62 are connected electrically and mechanically through the chip carrier 70.

As above-mentioned, a pad portion and an adhesion portion for the light transparent cover 67, etc., are indispensable to the chip carrier 70 composed of the solid state imaging element 61, and these portions determine the overall size of the device. Namely, the overall construction of the device has a large size, so that the size of the chip carrier 70 has to be larger than the size of the CCD element 66.

In the construction shown in FIG. 11, a prism 64 is disposed on the solid state imaging element 61 to define the diameter of the flexible tube, and the light receiving plane 71 of the CCD element 66 to receive the imaging light 65 is disposed at 90 degrees to the object being observed. However, the light receiving plane of the CCD element has been oriented directly toward the object. In this case, the prism is unnecessary, but the outer size of the device is determined by the size of the chip carrier, because the solid state imaging element has to be oriented vertically in the configuration of FIG. 11. Furthermore, it was necessary to bend the FPC assembled peripheral circuit components thereon 90 degrees, and to provide the FPC on the back side of the chip carrier 70. As a result, instances of deterioration of the FPC and damage or cutting of the wiring layers on the FPC were increased.

The miniaturization of the solid state imaging element itself has been advanced. As a result, the volume of the peripheral circuit components occupied in the solid state imaging device also has increased. Therefore, the width of the FPC becomes narrow as the size of the solid state imaging element decreases. The length of the FPC must be increased to assemble the peripheral components thereon.

SUMMARY OF THE INVENTION

An object of the present invention is to provide an improved solid state imaging device using a chip carrier having the same or a smaller size in comparison with the solid state imaging chip.

Another object of the present invention is to provide an improved solid state imaging device wherein the light receiving plane can be oriented toward the object being observed.

Another object of the present invention is to provide an improved solid state imaging device to increase the assembling density of the circuit board without enlarging the device.

The present invention is concerned with a solid state imaging device for detecting incident light from a predetermined direction relative to the device comprising, solid state imaging means including a light incident surface for receiving the incident light, and elongated printed circuit board means for alignment substantially parallel to the predetermined direction, the board means including means for supporting the imaging means and exposing the light incident surface directly to the incident light.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF PREFERRED EMBODIMENTS

Figure 1:
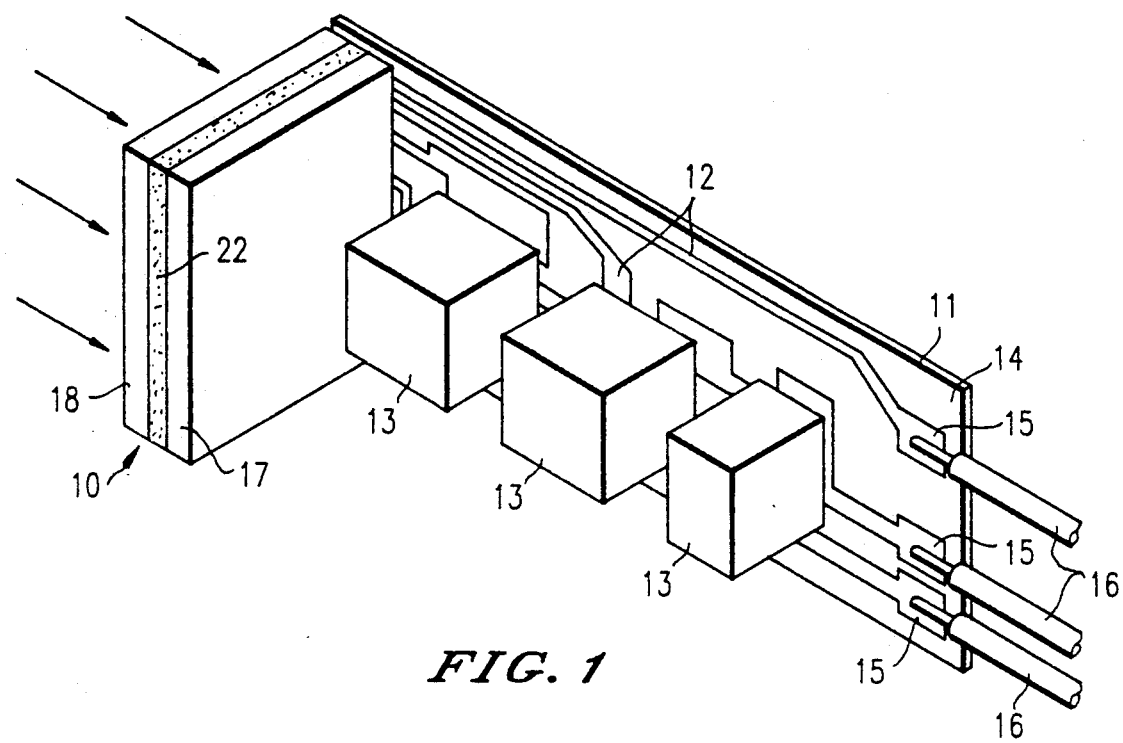
FIG. 1 is a perspective view illustrating first embodiment of the present invention.

Embodiments of the present invention will be explained referring to the drawings, wherein the same reference characters designate like or corresponding parts throughout.

Figure 2:
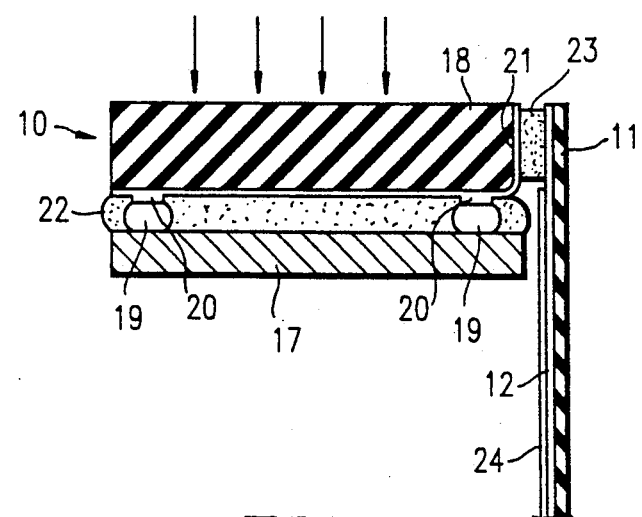
FIG. 2 is an expanded sectional view of the imaging element of FIG. 1.

FIGS. 1 and 2 illustrate a first embodiment of the present invention. A solid state imaging element 10 is disposed with its light receiving plane facing toward an object being observed. Thus, the element 10 can directly receive incident light (shown by the arrows). An FPC 11 is provided on the side of the solid state imaging element 10. Wiring patterns 12 are formed on the surface of the FPC 11. Plural chip components 13, e.g., a noise reduction circuit and a high frequency amplification circuit, are provided on the FPC 11 with wiring patterns 12 thereon. Connection pads 15 are formed on an end portion 14 of the FPC. Extension cables 16 are connected to these connection pads 15. The surface of the FPC 11 is covered by a protection film 24 made of polyimide resin.

The solid state imaging element 10 includes a CCD chip 17 and a light transparent cover 18 made of optical glass. The chip 17 and the cover 18 are connected by connection bumps 19. Connection bumps 19 are formed of solder, and In-Sn-Pb alloy is used in this embodiment. Connection bumps 19 are formed using a thermocompression bonding technique with alloy balls of 100 μm in diameter. These balls are bonded to Al pads provided on the surface of the CCD chip 17. Electrode patterns 20 are formed on the surface of the light transparent cover 18 using an evaporation technique. These electrode patterns 20 extend to a side surface 21 of the light transparent cover 18. The light transparent cover 18 is made of optical glass having an efficiency to pass almost 100 % visible light in the visible region.

The CCD chip 17 and the light transparent cover 18 are thermocompression bonded after positioning the connection pads 19 and the electrode patterns 20. An adhesive agent 22 made of light transparent resin, e.g., epoxy resin, is disposed between the CCD chip 17 and the light transparent cover 18. Namely, the adhesive agent is deposited on the CCD chip 17 prior to the thermocompression bonding. Thereafter, it is sealed therebetween by the thermocompression bonding. As another method, the adhesive agent may be soaked between the chip 17 and the cover 18 using a capillary phenomenon after the step of the thermocompression bonding. An acrylic resin being hardened by ultraviolet rays may be useful as the adhesive agent 22.

The electrode patterns 20 extend along the side surface 21 of the light transparent cover 18 and wiring patterns 12 provided on the surface of the FPC 11 are connected electrically and mechanically using an anisotropic electro-conductive film 23. The anisotropic electro-conductive film 23 is made by diffusing subminiaturized metal balls into the thermoplastic resin. The anisotropic electro-conductive film 23 is disposed between the side surface 21 of the light transparent cover 18 and the FPC 11, and is compression bonded at 180° C. As a result, electrode patterns 20 and wiring patterns 12 are electrically connected through miniaturized metal balls diffused into the thermoplastic resin. The remaining parts of the light transparent cover 18 and the FPC 11 other than electrode patterns 20 and wiring patterns 12 are connected only mechanically, because the metal balls do not contact therebetween, as compared with above-mentioned electrical connection.

In above-mentioned first embodiment of the present invention, the solid state imaging element 10 has been turned directly toward the object being observed without the need to bend the FPC 11. Furthermore, chip components 13 have been provided in the rear space of the solid state imaging element 10.

Electrode pads of the CCD chip 17 have been directly connected to electrode patterns 20 of the light transparent cover 18 through connection bumps 19. Thus, wire bonding has become unnecessary. As a result, parts of pads for bonding and parts for fixing the CCD chip and the light transparent cover have become unnecessary.

Namely, it has become very easy to use light transparent cover 18 and the CCD chip 17 of roughly the same size. This is because, the light transparent cover 18 has the chip carrier function and the CCD chip 17 is directly connected to electrode patterns formed on the light transparent cover 18. Therefore, the miniaturization and the lightening of the device construction can be achieved, in contrast to the case of using the chip carrier. The step of the wire bonding becomes unnecessary, and simplification of the manufacturing steps also can be accomplished.

Figure 3:
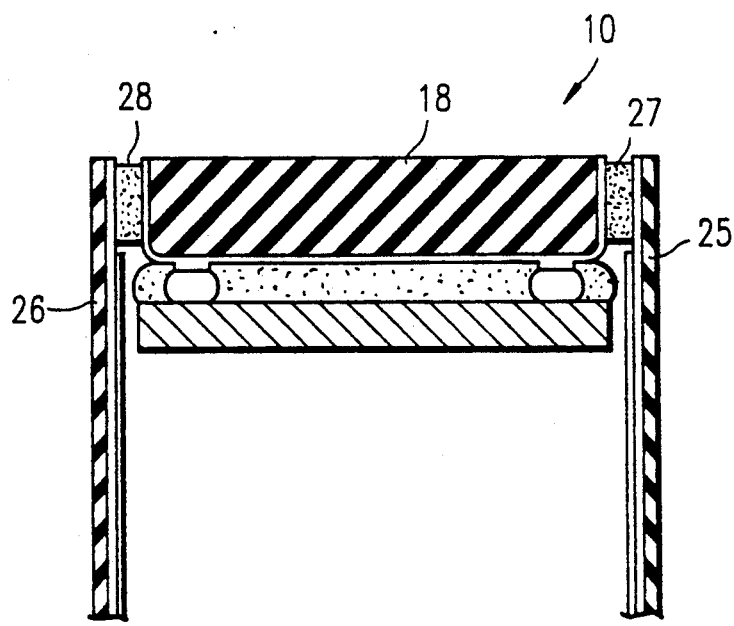
FIG. 3 is an expanded sectional view similar to FIG. 2 illustrating a second embodiment of the present invention.

FIG. 3 shows a second embodiment of the present invention. In this second embodiment, first and second FPCs 25 and 26 are connected on both sides of the light transparent cover 18 using first and second anisotropic electro-conductive films 27 and 28. This construction is useful when many chip components are assembled.

Figure 4:
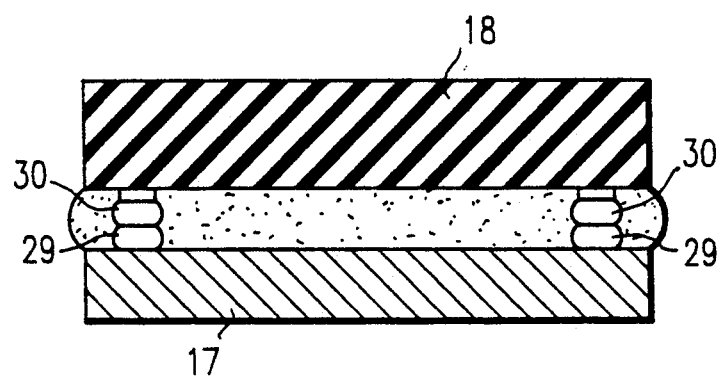
FIG. 4 is an expanded sectional view illustrating an imaging element of a third embodiment of the present invention.
Figure 5:
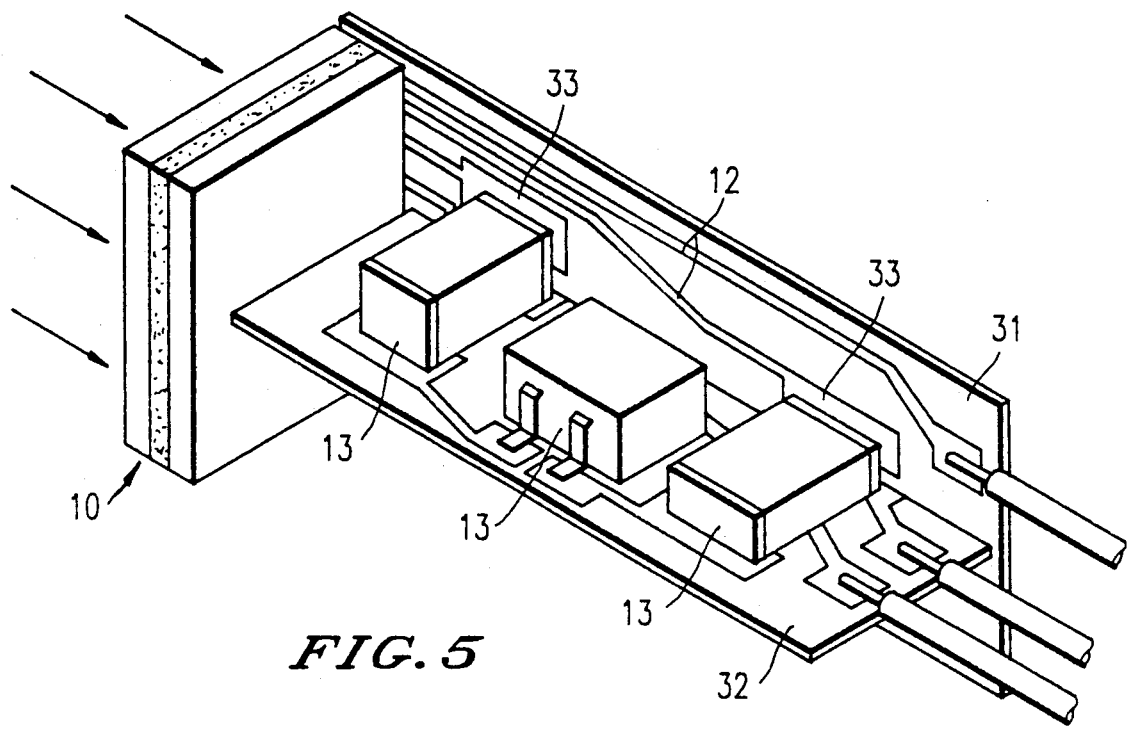
FIG. 5 is a perspective view illustrating a fourth embodiment of the present invention.

FIG. 4 shows a third embodiment of the present invention. In this third embodiment, connection bumps have a double layer construction. Namely, bumps 29 are formed on the CCD chip 17 using the wire bonding method. In family bumps 30 are formed on the light transparent cover 18. Thereafter, both bumps 29 and 30 are connected using the thermocompression bonding technique. This construction makes the connection between patterns of the CCD chip or the light transparent cover and the connection bumps easier FIG. 5 shows a fourth embodiment of the present invention. A first FPC 31 having wiring patterns 12 formed thereon is connected on the side of the solid state imaging element 10. A second FPC 32 assembled to the first FPC 31 meets the FPC 31 at a right angles. Namely, chip components 13 assembled on the second FPC 32 are connected by soldering on wiring patterns of the first FPC 31. In the other words, chip components 13 are strongly joined face to face to both FPCs 31 and 32.

This structure is useful for the high density assembling of many chip components without an increase in the lateral size of the whole device. In this embodiment, chip components 13 are assembled only on the one surface of the second FPC 32. However, these components may be assembled on both surfaces of the second FPC 32 when many components must be assembled thereon. Furthermore, in above-mentioned embodiment, only the second FPC 32 joins at a right angle to first FPC 31. However, this configuration may be modified, and several FPC's may be utilized.

Figure 6:
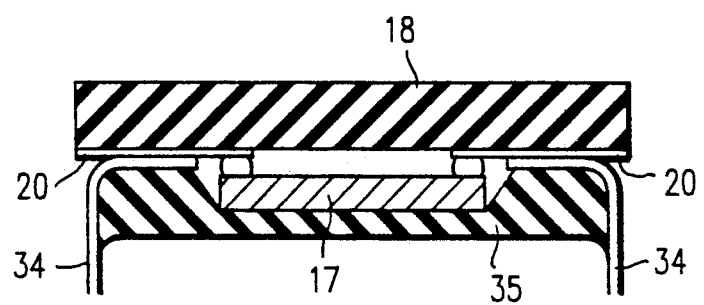
FIG. 6 is an expanded sectional view illustrating an imaging element of a fifth embodiment of the present invention.

FIG. 6 shows a fifth embodiment of the present invention. Tip portions bent 90 degrees of the leads 34 made of phosphor bronze are fixed on electrode patterns 20 provided on the surface of the light transparent cover 18. The back surface of the CCD chip 17 is sealed to the inside of leads 34 using an adhesive agent formed by a thermosetting resin into of an epoxy group. In this type of device, a ready-made socket is avarable, and its leads can be soldered directly on the printed circuit board.

Figure 7:
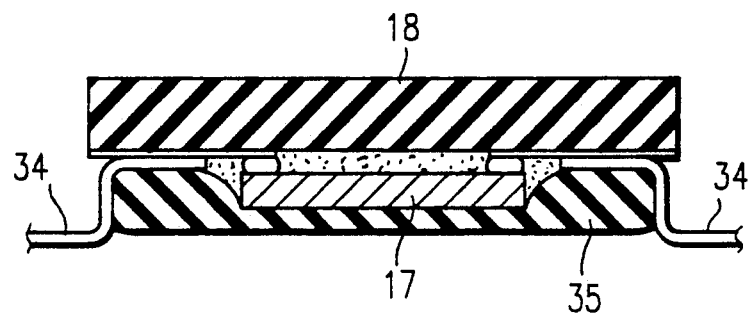
FIG. 7 is an expanded sectional view illustrating an imaging element of a sixth embodiment of the present invention.

FIG. 7 shows a sixth embodiment of the present invention. It is different to than the above-mentioned embodiment in that the tip portions of the leads are bent in two steps. As a result, the device is formed the flat-package type. In this device, leads 34 can be soldered directly on the printed circuit board too.

Figure 8:
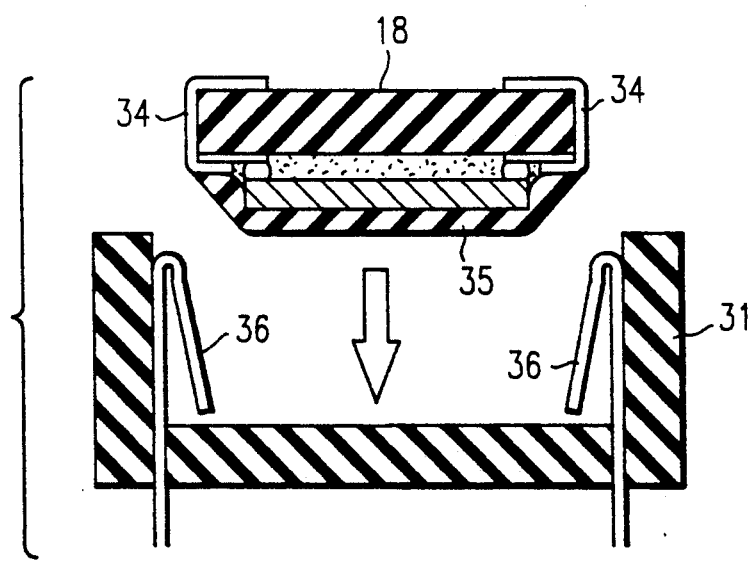
FIG. 8 is an expanded sectional view illustrating an imaging element of a seventh embodiment of the present invention.

FIG. 8 shows a seventh embodiment of the present invention. Leads 34 are bent surrounding from the side to top surfaces of the light transparent cover 18. This construction is strong mechanically. Further, this device can be used inserting directly into the socket having spring like leads 36.

Figure 9:
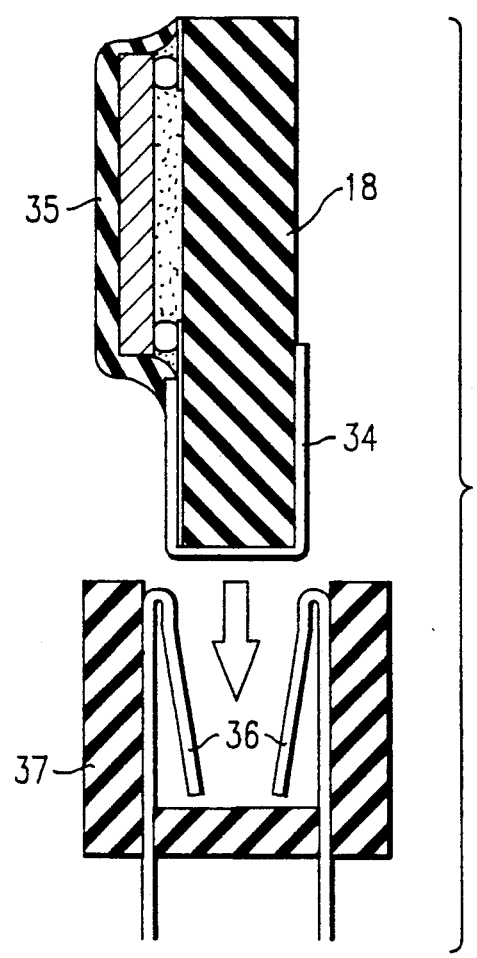
FIG. 9 is an expanded sectional view illustrating an imaging element of the present invention.

FIG. 9 shows an eighth embodiment of the present invention. Leads 34 are provided only on the one side of the light transparent cover 18. This type device is easy to especially change the device from the socket.

Figure 10:
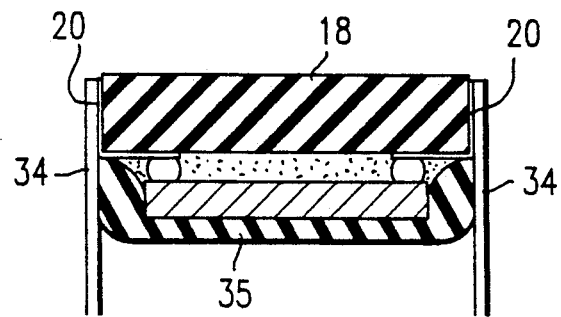
FIG. 10 is an expanded sectional view illustrating an imaging element of a ninth embodiment of the present invention.
Figure 11:
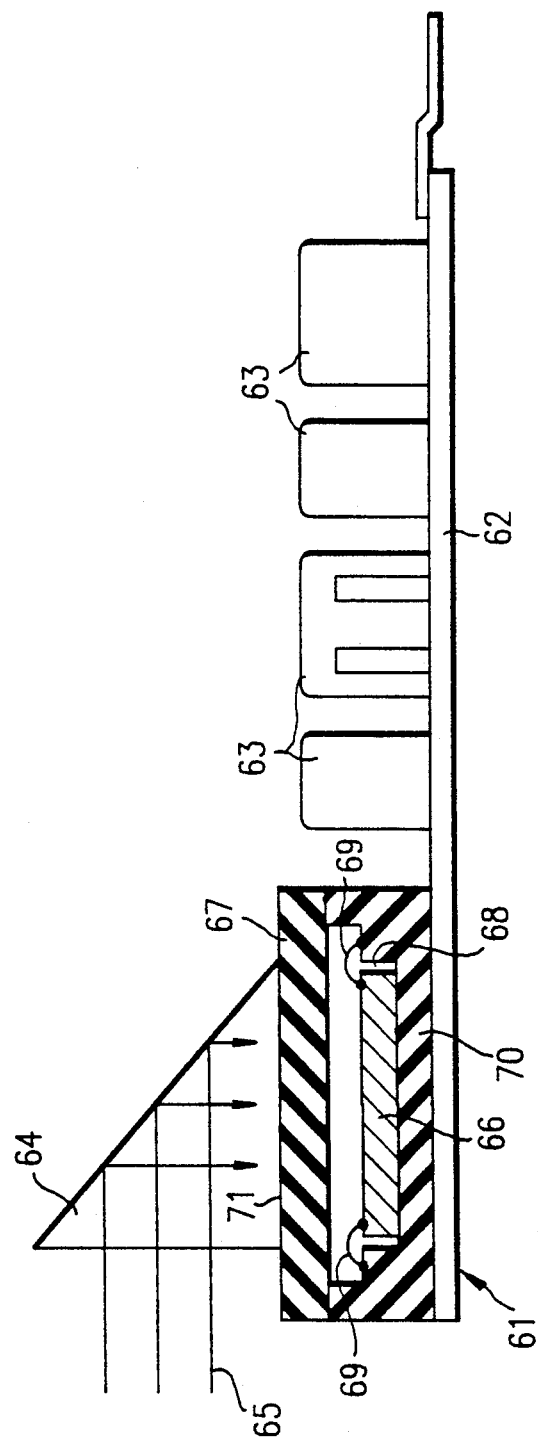
FIG. 11 is a sectional view illustrating a conventional solid state imaging device.

FIG. 10 shows a ninth embodiment of the present invention. Electrode patterns 20 are extended until the both side surfaces of the light transparent cover 18, and leads 34 are connected to electrode patterns 20 on the side surfaces of the light transparent cover 18.

What is claimed is:

1. A solid state imaging device for detecting incident light from a predetermined direction relative to the device, comprising:
    solid state image means including a light incident surface for receiving the incident light and a plurality of side surfaces each of said side surfaces being in a plane which is perpendicular to the plane of said incident light surface; and
    printed circuit board means connected using an electro-conductive anisotropic film to at least one of said side surfaces of the imaging means, and elongated in back of the light incident surface and perpendicular to said light incident surface.

2. A solid state imaging device, comprising:
    a light transparent cover having electro-conductive patterns thereon;
    a solid state imaging chip having a light receiving surface, and electrode patterns formed on the light receiving surface;
    connection bumps for connecting between the electro-conductive patterns of the light transparent cover and the electrode patterns of the imaging chip; and
    a light transparent resin between the light transparent cover and the solid state imaging chip.

3. The solid state imaging device of claim 2 wherein each connection bump includes multi-layers, each layer of the multi-layers including a different material.

4. The solid state imaging device of claim 2 wherein further comprises an adhesive agent for sealing on the back of the imaging chip.

5. The solid state imaging device of claim 4 wherein further comprises leads being connected to the electro-conductive patterns of the light transparent cover.

6. The solid state imaging device of claim 5 wherein each lead is bent with 90 degrees.

7. The solid state imaging device of claim 6 wherein each lead is additionally bent with 90 degrees.

8. The solid state imaging device of claim 7 wherein each lead is bent U-like groove surrounding on the light transparent cover.

* * * * *